United States Patent
Dahmen

(10) Patent No.: US 9,408,525 B2
(45) Date of Patent: Aug. 9, 2016

(54) OBJECTIVE LENS UNIT FOR ENDOSCOPES

(75) Inventor: Jan Dahmen, Seitingen-Oberflacht (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 236 days.

(21) Appl. No.: 13/293,471

(22) Filed: Nov. 10, 2011

(65) Prior Publication Data

US 2012/0123211 A1    May 17, 2012

(30) Foreign Application Priority Data

Nov. 11, 2010 (DE) .................... 10 2010 050 932

(51) Int. Cl.
| | | |
|---|---|---|
| *A61B 1/06* | (2006.01) | |
| *A61B 1/04* | (2006.01) | |
| *A61B 1/00* | (2006.01) | |
| *A61B 1/05* | (2006.01) | |
| *G02B 23/24* | (2006.01) | |

(52) U.S. Cl.
CPC ......... *A61B 1/00101* (2013.01); *A61B 1/00105* (2013.01); *A61B 1/00163* (2013.01); *A61B 1/05* (2013.01); *G02B 23/243* (2013.01)

(58) Field of Classification Search
CPC ................. A61B 1/00126; A61B 1/00121
USPC ................. 600/172, 175, 112, 129
See application file for complete search history.

(56) References Cited

U.S. PATENT DOCUMENTS

| | | | | |
|---|---|---|---|---|
| 5,228,430 A | * | 7/1993 | Sakamoto ............. A61B 1/05 348/65 |
| 5,512,036 A | | 4/1996 | Tamburrino et al. | |
| 5,562,640 A | * | 10/1996 | McCabe et al. ............... 604/541 |
| 5,609,561 A | | 3/1997 | Uehara et al. | |
| 5,961,445 A | * | 10/1999 | Chikama ...................... 600/112 |
| 6,095,970 A | | 8/2000 | Hidaka et al. | |
| 6,350,234 B1 | * | 2/2002 | Foerster-Klein ... A61B 1/00165 385/117 |
| 6,383,132 B1 | * | 5/2002 | Wimmer ...................... 600/159 |
| 6,554,767 B2 | | 4/2003 | Tanaka | |
| 8,529,440 B2 | * | 9/2013 | Terliuc ................... A61B 1/005 600/104 |
| 2005/0182299 A1 | * | 8/2005 | D'Amelio et al. ............ 600/175 |
| 2006/0291068 A1 | * | 12/2006 | Dahmen et al. ............... 359/643 |

(Continued)

FOREIGN PATENT DOCUMENTS

| | | |
|---|---|---|
| DE | 19806984 A1 | 8/1998 |
| DE | 102006017683 B3 | 8/2007 |

OTHER PUBLICATIONS

European Search Report; Application No. EP 11 18 7057; Issued: Mar. 8, 2012; Mailing Date: Mar. 19, 2012; 8 pages.

(Continued)

*Primary Examiner* — Matthew J Kasztejna
*Assistant Examiner* — Rynae Boler
(74) *Attorney, Agent, or Firm* — Whitmyer Group LLC

(57) ABSTRACT

An objective lens unit for endoscopes, with an objective lens having at least one lens and with an objective lens frame that is mounted in an endoscope housing in such a way that the insertion depth in the distal direction is restricted by a covering glass established in the endoscope housing and the objective lens frame that can be fastened in the endoscope housing forms the proximal end. In order to provide an objective lens unit for endoscopes that is simple to assemble and can be positioned in stationary manner in the endoscope housing, it is proposed according to the invention that the objective lens frame should be capable of being removably fastened in the endoscope housing.

11 Claims, 4 Drawing Sheets

(56) References Cited

U.S. PATENT DOCUMENTS

2007/0162095 A1\* 7/2007 Kimmel et al. ............... 607/102
2008/0027276 A1   1/2008 Rovegno
2010/0312186 A1\* 12/2010 Suchdev et al. ............... 604/131

OTHER PUBLICATIONS

German Search Report; Application No. 10 2010 050 932.9; Issued: Jun. 30, 2011; 5 pages.

\* cited by examiner

OBJECTIVE LENS UNIT FOR ENDOSCOPES

CROSS-REFERENCE TO RELATED APPLICATIONS

The present application claims priority of German patent application No. 10 2010 050 932.9 filed on Nov. 11, 2010, the content of which is incorporated herein by reference.

FIELD OF THE INVENTION

The invention relates to an objective lens unit for endoscopes, with an objective lens comprising at least one lens as well as with an objective lens frame that is thus mounted in an endoscope housing.

BACKGROUND OF THE INVENTION

Objective lens units of this type are known in the art in various embodiments. In order to adjust the objective lens in the longitudinal direction of the optical system on the one hand, and on the other hand to fasten the objective lens frame equipped with the objective lens in the endoscope housing in stationary manner, it is a familiar practice in the art to position the objective lens frame in the endoscope housing by means of a press-on element that, in turn, in the assembled state is non-separably cemented with the endoscope housing.

These known objective lens units have thoroughly proven themselves in the art; however, on the one hand, there is a risk of impurities from cementing the components and, on the other hand, there is no possibility of correcting after the fact a possible wrong positioning of the objective lens with respect to the optical axis, because the objective lens unit can no longer be dismantled.

SUMMARY OF THE INVENTION

It is consequently the object of the invention to provide an objective lens unit for endoscopes that is simple to assemble and can be positioned in the endoscope housing in stationary manner.

This object is fulfilled according to the invention in such a way that the objective lens frame can be separably fastened in the endoscope housing by at least one catch-lock connection.

As a result of the inventive separable arrangement of the objective lens frame in the endoscope housing, it becomes possible for the first time to dismantle the objective lens unit after the fact and to position the objective lens in the event of a possible erroneous position and to realign it in the correct position.

Inventive catch-lock connections are characterized in that they are simple to handle and guarantee a secure bonding of the components that are catch-locked to one another, while being simple and quick to separate again.

In order to prevent or to limit the pressure of the objective lens unit in the axial direction, that is, in particular in the direction toward the covering glass, so that the pressure is transmitted by the objective lens frame onto the objective lens that is connected with the objective lens frame, it is proposed according to a first embodiment of the invention that the insertion depth of the objective lens unit into the endoscope housing can be restricted in the distal direction by a stop for the objective lens frame.

According to an inventive embodiment, the stop is configured as an overhang in the endoscope housing, which the objective lens frame runs up against in the distal end position.

With an alternative embodiment of the invention, it is proposed that the stop should be configured as a catch-lock connection by which the objective lens frame can be separably secured in the endoscope housing. In this practical embodiment, two advantages are immediately provided by means of the catch-lock connection, namely the separable mounting of the objective lens frame in the endoscope housing and the restriction of the insertion depth of the objective lens unit into the endoscope housing.

With a first embodiment for configuring the inventive separable catch-lock connection, it is proposed that the catch-lock connection should consist of at least one catch-lock element positioned on the objective lens frame and at least of one catch-lock recess configured in the endoscope housing for receiving a catch-lock element each time.

Here, the catch-lock element is advantageously positioned on the spring-elastically-configured proximal end of the objective lens frame. The spring-elasticity of the proximal end of the objective lens frame ensures that the catch-lock element engages automatically into the corresponding catch-lock recess as soon as the two components are brought into congruence with one another.

Alternatively, the at least one catch-lock element, configured for example as a rod or sphere, can also be positioned in the endoscope housing and the catch-lock recess can be positioned on the objective lens frame.

In addition, for the first embodiment of the invention, it is proposed that the catch-lock connection should be capable of being fastened in the catch-locked position by a holding element that can be inserted into the objective lens frame from the proximal side, so that the at least one catch-lock element is pressed radially outward by the holding element into the corresponding catch-lock recess. The catch-lock element is fastened in stationary manner in the catch-lock recess by means of the radial press-on force of the holding element.

To release the catch-lock connection for the first embodiment of the invention, it is proposed that the spring-elastic proximal end of the objective lens frame should be capable of bending radially inward by means of a dismantling tool that can be inserted from the proximal side into the endoscope housing. In using the holding element to fasten the catch-lock connection, said holding element of course must first be removed from the objective lens frame.

To release the catch-lock connection, in which the catch-lock element is positioned in the endoscope housing and the catch-lock recess is positioned on the objective lens frame, it is proposed that the catch-lock element should be capable of being pressed radially outward into the endoscope housing by means of a dismantling tool that can be applied from the proximal side onto the objective lens frame.

Finally, with a third embodiment for configuring the inventive separable catch-lock connection, it is proposed that the objective lens frame should be capable of being separably fastened by means of a press-on unit, which pressures the objective lens frame in the distal direction; here the press-on unit advantageously consists of a spring element configured as a pressure spring and of an abutment for the pressure spring, and the abutment can be separably fastened on the endoscope housing by means of at least one catch-lock connection. Use of the pressure spring in the press-on unit serves to press the objective lens frame in the distal direction against the overhang in the endoscope housing and thus to position the objective lens, which is connected with the objective lens frame, in the axial direction in a stationary manner in the endoscope housing.

To configure the abutment, it is proposed with the invention that said abutment should be configured as a slotted spring-elastic sheath, such that the distal border of the sheath comprises a surrounding catch-lock protrusion, which in assembled condition engages into a surrounding catch groove in the endoscope housing to configure the separable catch-lock connection. The abutment section, with which the spring element is directly contiguous, is the proximal section of the sheath, which is configured as a portion of a ring.

Finally, it is proposed with the invention that the sheath should be configured to taper conically in the proximal direction, so that a dismantling tube can be slid onto the conical outer wall of the sheath to release the catch-lock connection between the sheath and the endoscope housing, so that the spring-elastic sheath is compressed radially inward by its proximal ring portion until the surrounding catch-lock protrusion goes out of engagement with the catch groove configured in the endoscope housing.

Further properties and advantages of the invention can be seen from the appended drawings, in which five embodiments of an inventive objective lens unit for endoscopes are illustrated merely as examples, without restricting the invention to these embodiments.

DETAILED DESCRIPTION OF THE INVENTION

Figure 1:
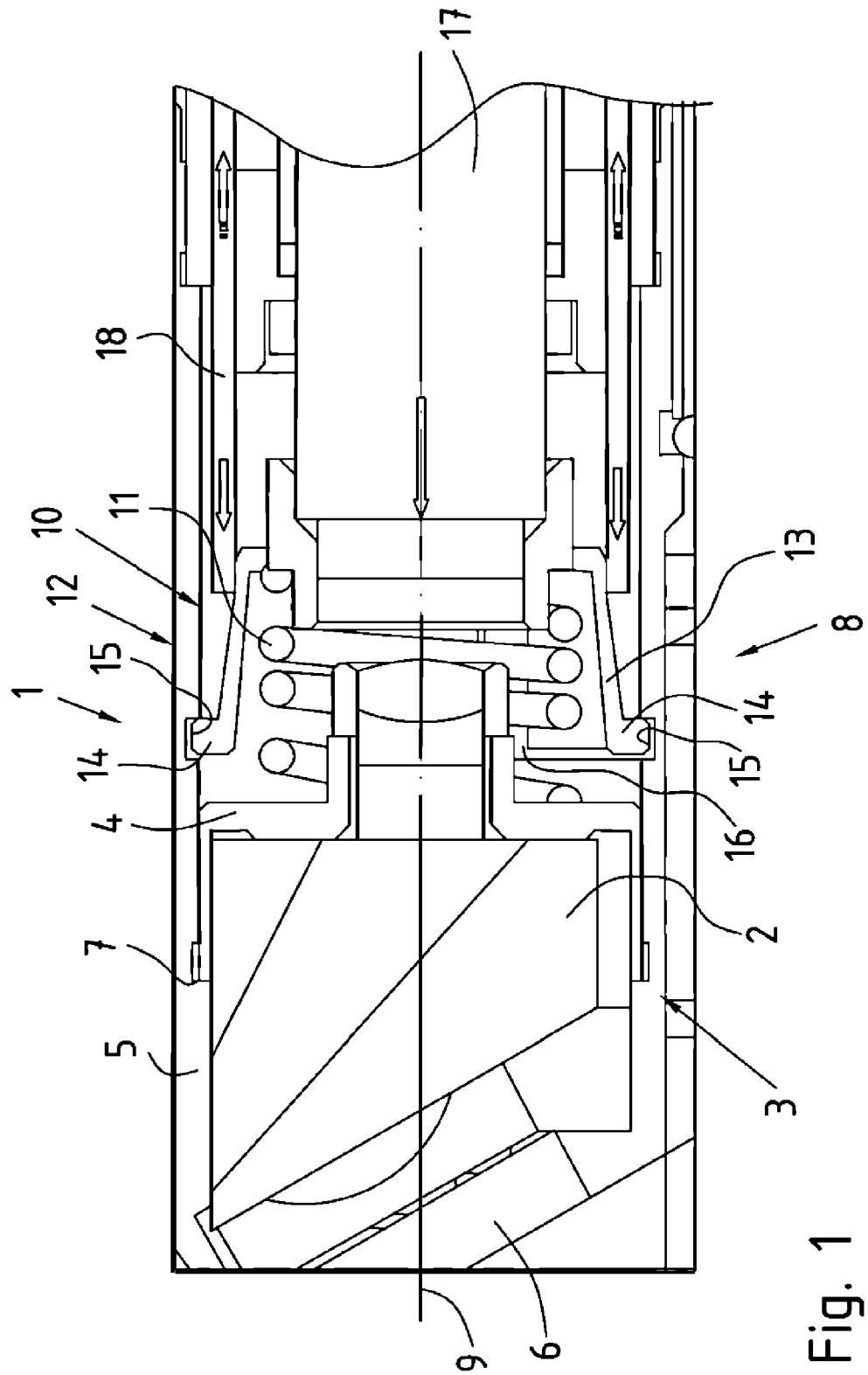
FIG. 1 shows a longitudinal section through a first embodiment of an inventive objective lens unit.

The objective lens units 1 for endoscopes, illustrated in FIGS. 1 through 4, consist essentially of an objective lens 3 comprising at least one lens 2, as well as of an inventive lens frame 4, whereby the objective lens unit 1 is mounted in an endoscope housing 5 in such a way that the objective lens unit 1 is positioned on the distal end leaving an aerial space from a covering glass 6 fastened in the endoscope housing 5 and so that the objective lens frame 4 that can be fastened in the endoscope housing 5 forms the proximal end of the objective lens unit 1.

Figure 2:
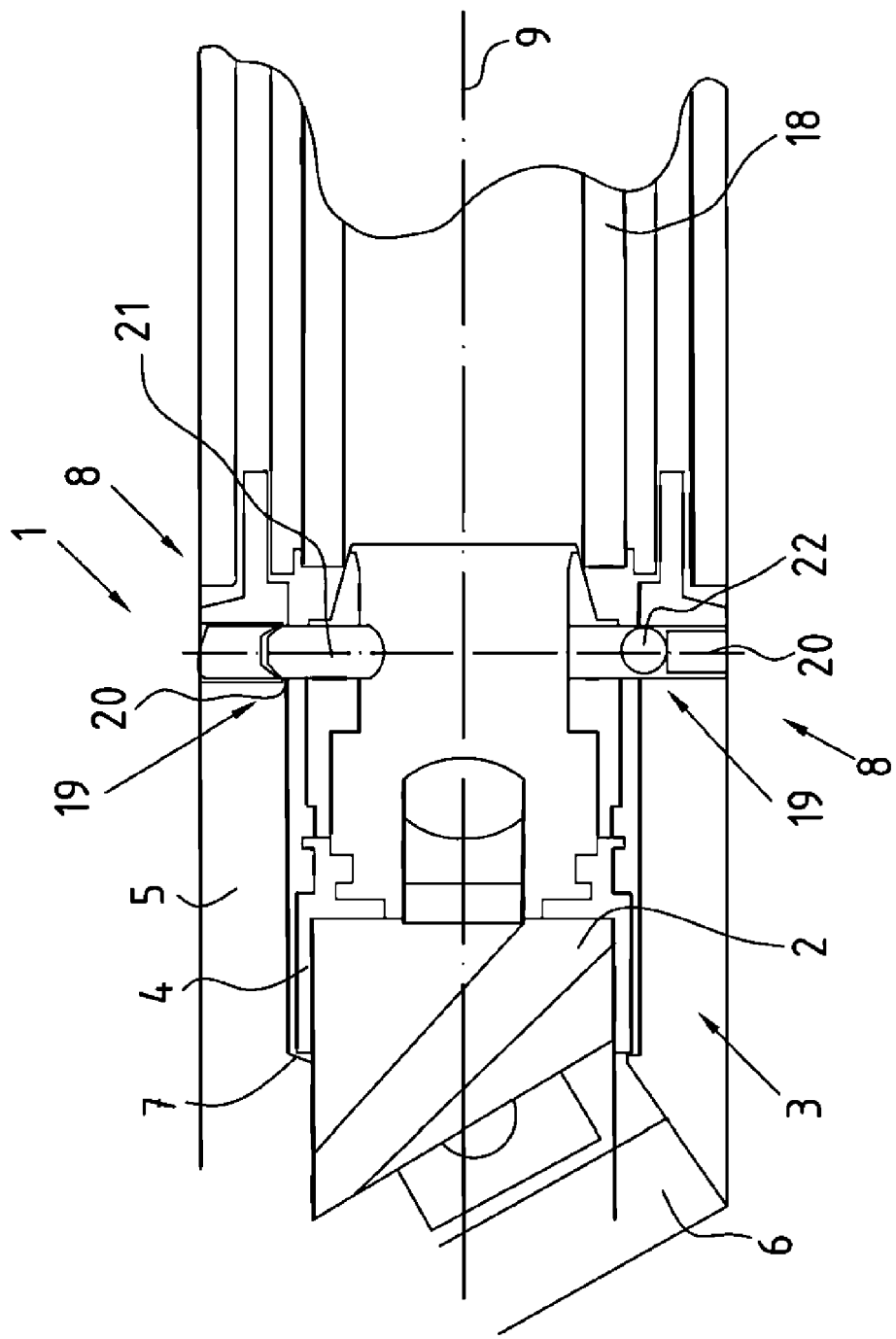
FIG. 2 shows a longitudinal section through a second and third embodiment of an inventive objective lens unit.
Figure 3:
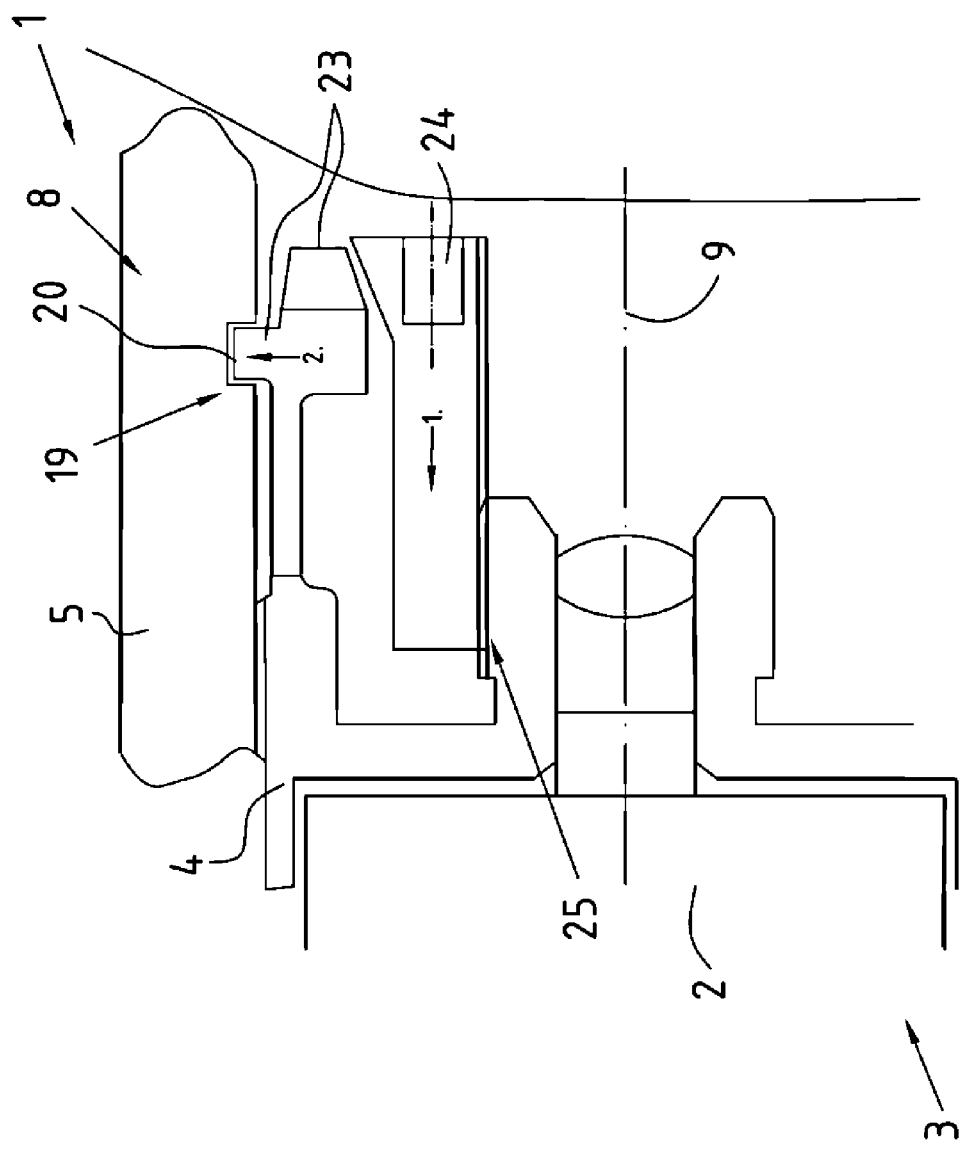
FIG. 3 shows a longitudinal section through a fourth embodiment of an inventive objective lens unit.

To restrict the insertion depth of the objective lens unit 1 into the endoscope housing 5 in the distal direction, in the embodiments illustrated in FIGS. 1 through 3 a stop in the form of an overhang 7 is configured in the endoscope housing 5, and the objective lens frame 4 connected with the objective lens 3, for example by cementing, is contiguous with said stop upon insertion into the endoscope housing 5 and thus, on the one hand, further insertion in the distal direction is prevented, so that pressure on the optical components of the objective lens unit 1 is avoided, and, on the other hand, precisely located installation of the object lens 3 is ensured.

Figure 4:
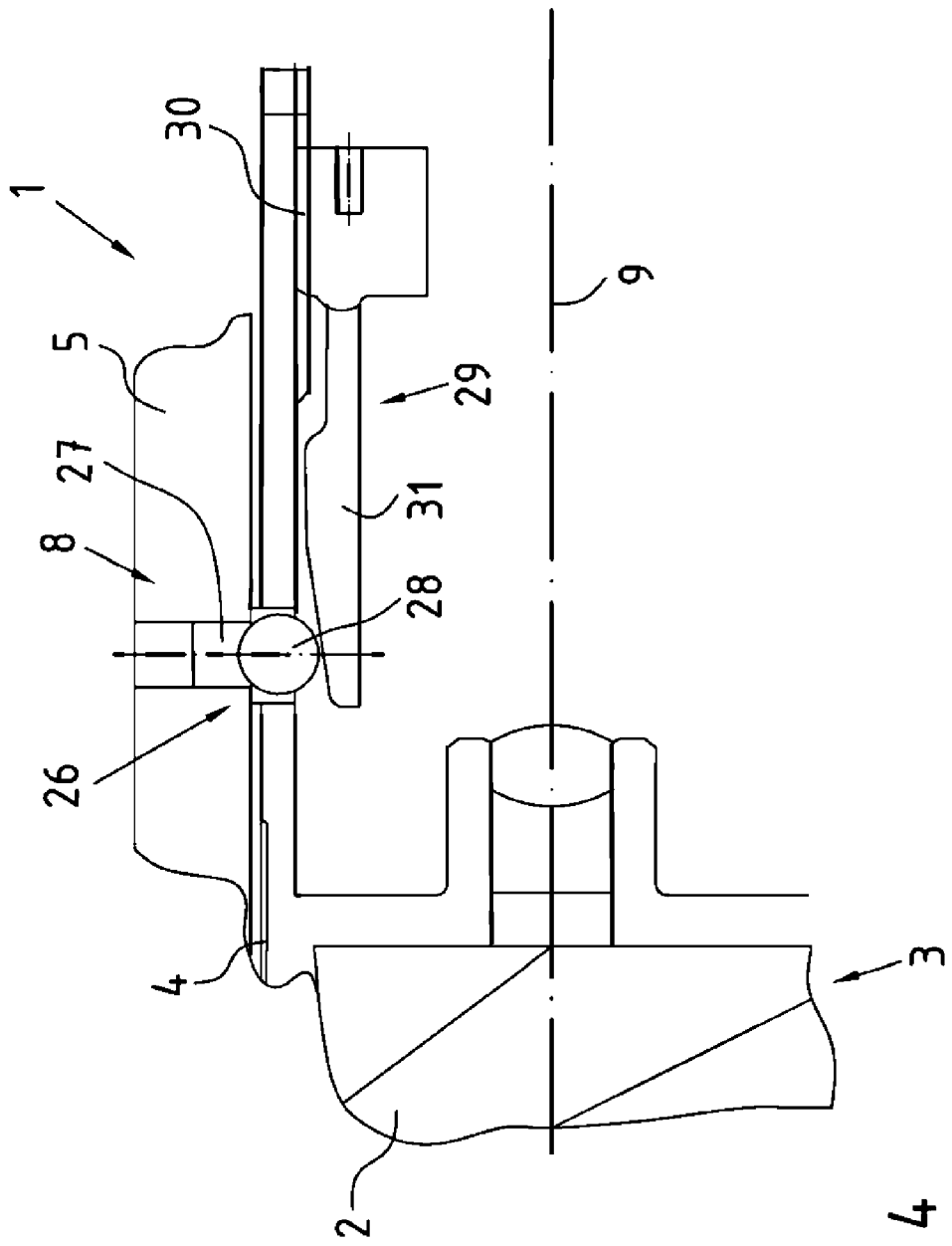
FIG. 4 shows a longitudinal section through a fifth embodiment of an inventive objective lens unit.

Alternatively and/or in addition, the insertion depth of the objective lens unit 1 in the distal direction into the endoscope housing 5 in the embodiments illustrated in FIGS. 2 through 4 is restricted by a catch-lock connection 8, by means of which the objective lens frame 4 that guides the objective lens 3 on the proximal end can be separably fastened in the endoscope housing 5. As soon as the catch-lock connection 8 is locked while inserting the objective lens frame 4 into the endoscope housing 5 and thus the objective lens frame 4 and the endoscope housing 5 are fixed with respect to one another, the objective lens 3 connected with the objective lens frame 4 cannot be inserted any further in the distal direction into the endoscope housing 5.

Use of the catch-lock connection 8 for fastening the objective lens frame 4 in the endoscope housing 5 has in addition the advantage that the objective lens unit 1 is easy to install and to dismantle again. The successive capacity to dismantle the objective lens unit 1, in fact, constitutes an essential advantage over the state of the art, because for example faulty alignments of the objective lens 3 with respect to the optical axis 9 are correctible and impurities that can collect upon cementing the conventional objective lens units 1 are completely excluded.

The embodiments illustrated in FIGS. 1 through 4 are distinguished from one another by the configuration of the objective lens frame 4 as well as of the catch-lock connections 8 for separable mounting of the objective lens frames 4 in the endoscope housings 5.

In the first embodiment, illustrated in FIG. 1, the objective lens frame 4 can be separably fastened in the endoscope housing 5 by a press-on unit 10, which presses the objective lens frame 4 and thus also the objective lens 3 connected with the objective lens frame 4 in the distal direction, and the press-on unit 10 consists of a spring element configured as a pressure spring 11 as well as an abutment 12 for the pressure spring 11 that can be fastened on the endoscope housing 5 by means of the catch-lock connection 8.

Use of the pressure spring 11 in the press-on unit 10 serves to press the objective lens frame 4 in the distal direction against the overhang 7 in the endoscope housing 5 and thus to position the objective lens 3 connected with the objective lens frame 4 in the axial direction in a stationary manner in the endoscope housing 5.

As can be further seen in FIG. 1, the abutment 12 is configured as a slotted spring-elastic sheath 13, such that the distal edge of the sheath 13 comprises a surrounding catch-lock protrusion 14 that, in installed condition, engages in a surrounding catch groove 15 in the endoscope housing 5 in order to form the separable catch-lock connection 8. On the proximal end, the sheath 13 is configured to taper conically. The spring elasticity of the sheath 13 is achieved by means of slits that are configured from the distal end of the sheath 13 heading in the axial direction of the sheath 13.

The spring elasticity of the sheath 13 serves to allow the sheath 13 to be pressed together radially toward the inside upon insertion in the endoscope housing 5 and serves to allow the surrounding catch-lock protrusion 14 to engage automatically in the catch-lock groove 15 configured in the endoscope housing 5 upon reaching the corresponding position because of the expansion of the sheath 13 in the radial direction, in order to fix the abutment 12 and thus the objective lens frame 4 or the entire objective frame unit 1 as well, in the axial direction in the endoscope housing 5.

As shown in FIG. 1, to insert the objective lens unit 1 into the endoscope housing 5, an installation pin 17 can be used that can be applied to the sheath 13 from the proximal end.

To release the catch-lock connection 8 and thus to dismantle the objective lens unit 1, a dismantling tool 18, which is configured as a tube for instance, can be slid on the conical outer wall of the sheath 13 between the sheath 13 and the endoscope housing 5, so that the spring-elastically configured sheath 13 is pressed together radially inward until the surrounding catch-lock protrusion 14 goes out of engagement with the catch-locking groove 15 configured in the endoscope housing 5.

In the embodiments illustrated in FIGS. 2 and 3, the catch-lock connection 8 consists of at least one catch-lock element 19 positioned on the objective lens frame 4 and at least one catch recess 20 configured in the endoscope housing 5 to receive in each case one catch-lock element 19, such that the at least one catch-lock element 19 is positioned on the spring-elastically configured proximal end of the objective lens frame 4. Here the catch-lock recess 20 is configured in the form of a borehole.

The spring-elastic configuration of the proximal end of the objective lens frame 4 serves to allow the objective lens frame 4 to be pressed together radially inward upon insertion into the endoscope housing 5 and, upon reaching the corresponding position, allows the at least one catch-lock element 19 to engage automatically in the catch-lock recess 20 configured in the endoscope housing 5 because of the expansion of the objective lens frame 4 in the radial direction, in order to fix the objective lens frame 4 or the entire objective lens unit 1 without free play in the axial direction in the endoscope housing 5. Rotational fixing is likewise ensured, because the catch-lock recess 20 or recesses 20 are configured on concrete peripheral positions of the endoscope housing 5.

As can be seen from FIG. 2, to release the catch-lock connection 8 and thereby to dismantle the objective lens unit 1, a dismantling tool 18, configured for instance as a tube, can be slid onto the spring-elastic proximal end of the objective lens frame 4, so that the spring-elastically configured proximal end of the objective lens frame 4 is pressed together radially inward until the at least one catch-lock element 19 goes out of engagement with the catch-lock recess 20 configured in the endoscope housing 5.

To configure the at least one catch-lock element 19 that is positioned on the spring-elastic proximal end of the objective lens frame 4, two embodiments are illustrated in FIG. 2, namely the configuration of the catch-lock element 19 as a pin 21—in the upper part of FIG. 2—or as a sphere 22—in the lower part of FIG. 2.

In the fourth embodiment, illustrated in FIG. 3, the at least one catch-lock element 19 of the catch-lock connection 8 is configured as a latch 23 that is formed on the spring-elastic end of the objective lens frame 4 and engages by catching in the corresponding catch-lock recess 20 in the endoscope housing 5. In this embodiment the catch-lock recess 20 is preferably configured as a ring-shaped catch-lock recess, for example as a ring groove 20.

In addition, FIG. 3 shows that the catch-lock connection 8 can be rotationally fixed, particularly in the catch position, by means of a holding element 24 that can be inserted from the proximal end into the objective lens frame 4. In the illustrated embodiment, the holding element 24 can be fastened to the objective lens frame 4 by a threaded connection 25.

The holding element 24 is essentially tubular in shape and widens conically in the proximal direction. Alternatively or in addition, the side of the objective lens frame 4 that faces the holding element can be configured conically in the area of the latch 23.

Owing to the radial pressure force of the holding element 24, the catch-lock element 19 is fixed in stationary manner and friction-locked in the catch-lock recess 20. As a result, a rotational fixing can thus be established, in this case a friction-locked connection—instead of a form-fitting connection as in the preceding embodiment.

In the fifth embodiment, illustrated in FIG. 4, the catch-lock connection 8 consists of at least one catch-lock element 26 positioned in the objective lens frame 4 and at least one catch-lock recess 27 configured in the endoscope housing 5 to receive in each case one catch-lock element 26; here the catch-lock element 26 is configured by way of example in the illustrated embodiment as a sphere 28, although other configurations are also possible. The catch-lock recess 27, as in the preceding embodiments, can be configured as a ring groove or else as a borehole or boreholes on one or more concrete peripheral positions on the endoscope housing 5.

In addition, FIG. 4 shows that the catch-lock connection 8 can be moved into the catch-lock position and can be fixed in said position by means of a holding element that can be inserted from the proximal end into the objective lens frame 4, and that the sphere 28 is pressed radially outward into the corresponding catch-lock recess 27 by the holding element 29. In the illustrated embodiment, the holding element 29 can be fastened to the objective lens frame 4 by a threaded connection 30. Owing to the radial press-on force of the holding element 29, the sphere 28 is fixed in stationary manner and friction-locked in the catch-lock recess 27. As a result, in addition to the axial securing of the objective lens frame 4 in the endoscope housing 5, rotational fixing is also ensured. This occurs, first of all, because the catch-lock recess 27 is configured in the shape of the ring groove and the connection between the catch-lock element 26 and the catch-lock recess 27 is sufficiently friction-locked in the holding element 29 that is screwed in for the catching position. It occurs, secondly, because the catch-lock recess 27 is configured in the form of the concrete peripheral position or positions of the endoscope housing 5.

In the illustrated embodiment of the holding element 29, the sphere 28 is pressed into the catch-lock recess 27 in the endoscope housing by a spring-elastic press-on arm 31. The spring force of the press-on arm 31 acting on the sphere 28 is increased or reduced depending on the screw-in depth of the holding element 29 into the objective lens frame 4. This occurs because the press-on arm 31 is configured as a segment of a sheath that widens in the proximal direction.

To release the catch-lock connection 8 and thus to dismantle the objective lens unit 1, the holding element 29 is screwed out of the objective lens frame 4, so that the sphere 28 falls radially inward out of the catch-lock recess 27 and the catch-lock connection 8 is cancelled. The objective lens unit 1 can be drawn thereafter in the proximal direction out of the endoscope housing 5.

The objective lens units 1 configured as described in the foregoing are characterized in that they can be fastened in the endoscope housing 5 so that they are removable and thus capable of dismantling.

What is claimed is:

1. An endoscope, comprising
a cover glass fastened directly to an endoscope housing at a distal end of the endoscope,
an objective lens unit comprising an objective lens and an objective lens frame,
the objective lens having at least one lens,
the objective lens frame mounted within the endoscope housing proximate to the cover glass, the objective lens frame forming a proximal end of the objective lens unit, and
a catch-lock connection removably fastening the objective lens frame within the endoscope housing at the distal end of the endoscope, the catch-lock connection comprising at least one catch-lock element positioned on a proximal end of the of the objective lens frame, the catch-lock element being spring-elastically configured such that the catch-lock element engages automatically into at least one catch-lock recess formed in the endoscope housing upon the catch-lock element and the catch-lock recess aligning with each other.

2. The endoscope according to claim 1, wherein an insertion depth of the objective lens into the endoscope housing is restricted in the distal direction by a stop for the objective lens frame.

3. The endoscope according to claim 2, wherein the stop is configured as an overhang in the endoscope housing, with which the objective lens frame is contiguous in the distal end position.

4. An endoscope, comprising
a cover glass fastened directly to an endoscope housing at a distal end of the endoscope,
an objective lens unit comprising an objective lens and an objective lens frame,
the objective lens having at least one lens,
the objective lens frame mounted within the endoscope housing proximate to the cover glass, the objective lens frame forming a proximal end of the objective lens unit, and
a catch-lock connection removably fastening the objective lens frame within the endoscope housing at the distal end of the endoscope, the catch-lock connection comprising a catch-lock element positioned on a proximal end of the of the objective lens frame, the catch-lock element being spring-elastically configured such that the catch-lock element engages automatically into a catch-lock recess formed in the endoscope housing upon the catch-lock element and the catch-lock recess aligning with each other,
wherein the objective lens frame is separably fastened in the endoscope housing by a press-on unit, and said press-on unit pressures the objective lens frame in a distal direction.

5. The endoscope according to claim 4, wherein the press-on unit comprises a spring element and an abutment for the spring element, the spring element being configured as a pressure spring, the abutment being separably fastened to the endoscope housing, and the abutment comprising the catch-lock element.

6. The endoscope according to claim 5, wherein the abutment is separably fastened to the endoscope housing by the catch-lock connection.

7. The endoscope according to claim 5, wherein the abutment is configured as a slotted spring-elastic sheath.

8. The endoscope according to claim 7, wherein a distal edge of the sheath comprises the catch-lock element that, in assembled state, engages in the catch-lock recess in the endoscope housing.

9. The endoscope according to claim 7, wherein the sheath is configured as conically tapering in a proximal direction.

10. The endoscope according to claim 9, wherein to release the catch-lock connection between the sheath and the endoscope housing, a dismantling tube is slidable onto a conical outer wall of the sheath.

11. The endoscope according to claim 1, wherein the objective lens frame is mounted entirely within the endoscope housing proximate to the cover glass.

* * * * *